United States Patent
Peuker et al.

(10) Patent No.: US 6,543,611 B1
(45) Date of Patent: Apr. 8, 2003

(54) MIXER CAPSULE

(75) Inventors: Marc Peuker, Seefeld (DE); Angela Stenger, Grünwald (DE); Martin Hartung, München (DE); Gabriele Hager, Augsburg (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/856,528

(22) PCT Filed: Nov. 19, 1999

(86) PCT No.: PCT/DE99/03701

§ 371 (c)(1),
(2), (4) Date: May 23, 2001

(87) PCT Pub. No.: WO00/30953

PCT Pub. Date: Jun. 2, 2000

(30) Foreign Application Priority Data

Nov. 26, 1998 (DE) .................................... 298 21 193 U

(51) Int. Cl.⁷ ............................................... B65D 25/08
(52) U.S. Cl. ...................................... 206/219; 206/63.5
(58) Field of Search ........................ 206/63.5, 219–220, 206/222; 215/DIG. 8; 366/602; 222/136

(56) References Cited

U.S. PATENT DOCUMENTS

| | | | | | |
|---|---|---|---|---|---|
| 2,487,236 A | * | 11/1949 | Greenberg | ................... | 206/220 |
| 3,655,035 A | * | 4/1972 | Muhlbauer | ................... | 206/219 |
| 3,888,113 A | | 6/1975 | Miranda | | |
| 4,136,775 A | * | 1/1979 | Zaltsman | ................... | 206/219 |
| 4,182,447 A | * | 1/1980 | Kay | ................... | 206/220 |
| 4,362,242 A | * | 12/1982 | Cheetham | ................... | 206/219 |
| 4,640,424 A | * | 2/1987 | White | ................... | 215/11.1 |
| 4,863,017 A | * | 9/1989 | Vlock | ................... | 206/219 |
| 4,941,751 A | * | 7/1990 | Muhlbauer | ................... | 206/217 |
| 5,064,306 A | * | 11/1991 | Gueret | ................... | 401/133 |
| 5,088,830 A | * | 2/1992 | Muhlbauer | ................... | 366/108 |
| 5,199,808 A | * | 4/1993 | Gueret | ................... | 401/133 |
| 5,967,308 A | * | 10/1999 | Bowen | ................... | 206/219 |
| 6,386,872 B1 | * | 5/2002 | Mukasa et al. | ............. | 206/219 |

FOREIGN PATENT DOCUMENTS

| | | |
|---|---|---|
| DE | 36 35 574 A | 4/1988 |
| DE | 39 20 537 A | 2/1990 |
| DE | 93 032 68 U | 7/1994 |
| EP | 783 872 A | 7/1997 |

OTHER PUBLICATIONS

PCT Search Report (PCT/ISA/210 mailed Jun. 7, 2000).

* cited by examiner

Primary Examiner—Shian Luong
(74) Attorney, Agent, or Firm—Crowell & Moring LLP

(57) ABSTRACT

A mixer capsule, especially for the production of dental materials, comprising a cartridge (10) that is closed on one end by a piston (12). The piston has a hemispherical recess (12) that forms a chamber and is closed off from the main chamber (18) of the cartridge (10) by means of a separating device (16). A body (20) that is provided in the initial state in the main chamber (18) is used to facilitate the mixing process and to penetrate the separating device (16) at the beginning of the process, whereby the main chamber (18) and the subsidiary chamber (17) form a single mixing area. At the end of the output process, the body (20) enters the hemispherical subsidiary chamber (17) and acts as a displacer.

15 Claims, 1 Drawing Sheet

MIXER CAPSULE

Figure 1:
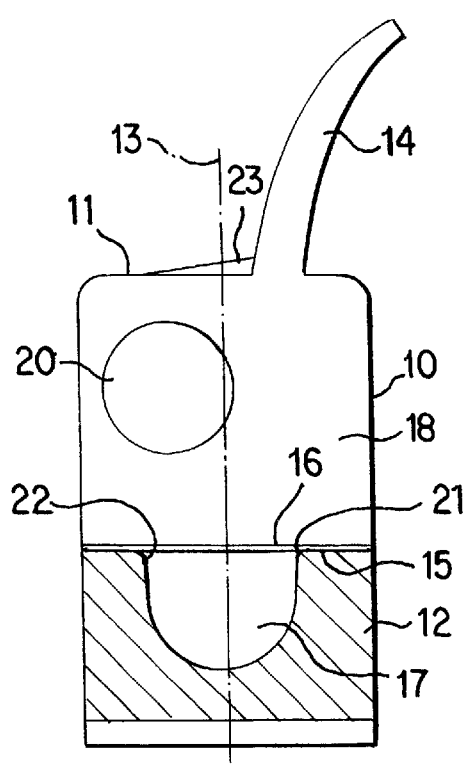

The present invention relates to a mixer capsule and a mixer unit which includes a mixer capsule, in particular for the production of a dental material.

Mixer capsules which are filled with two or more components in separate chambers by the manufacturer are used to produce mixtures of the components. The components are brought into communication and mixed with one another by the user, for example by the destruction of a wall separating the chambers.

Mixer capsules for the production of dental materials which are often mixed from a pulverulent component and a liquid component, the mixing operation usually taking place in a shaker unit, are known in the dental sector. The fully mixed substance is then discharged directly onto the working area, for example into a tooth cavity, through a discharge spout formed integrally on the mixer capsule.

DE 36 35 574 has disclosed a mixer capsule which is intended for the production of jointing and sealing compounds. In an exemplary embodiment described in this document, an auxiliary chamber which is present in the discharge piston is delimited, on the side which faces the main chamber of the capsule, by a sheet and, on the opposite side, by an auxiliary piston which is arranged displaceably in the discharge piston. In the starting state of the mixer capsule, as well as the second component, a mixer body is accommodated in the auxiliary chamber, which body initially serves to destroy the sheet by manual displacement of the auxiliary piston and then assists with the mixing operation. To allow the reduction in volume which is necessary for displacement of the inner piston together with ball, a gas cushion is provided in the mixing chamber.

In a further embodiment of the known mixer capsule, the mixer ball is initially situated in the main chamber. In this case, the auxiliary chamber which is present in the piston is closed off from the main chamber by means of a cover and on its rear side by a bellows. As a result of manual pressure being applied to the bellows, the cover is pressed away from the piston, so that the two chambers are brought into communication for the purpose of activation of the capsule.

In both cases, a dedicated working step which has to be carried out manually is required for activation of the capsule. Furthermore, a gas cushion is required in order to allow the reduction in volume which is required for removal of the cover.

In a multicomponent mixer capsule for dental purposes which is known from DE 94 00 374 U1, a first component is contained in a mixing chamber and a second, liquid component is contained in a film bag which is arranged in an auxiliary chamber which is separated from the mixing chamber by a displaceable wall element. A cylindrical mixing body which is present in the mixing chamber is used to displace the wall element at the start of the mixing operation and thus to compress the film bag, so that the latter bursts open and releases the liquid component through a liquid passage which is present in the wall element.

One difficulty of this device consists in designing the wall element, the film bag and the capsule itself in such a way and in dimensioning these components with sufficiently low tolerances for the wall element to be held in its starting position while the capsule is being stored and transported but to be displaced sufficiently far and with such force, under the action of the mixing body, that the film bag bursts open. In this context, it should be borne in mind that the fact that the film bag is often only partially emptied leads to undesirable changes in the mixing ratio and therefore to deterioration in the properties of the finished mixture. Another drawback is that this arrangement is only suitable for mixing, but not for application of the paste.

DE 93 03 268 U1 describes a multicomponent mixer capsule with ejection device for a mixed compound, primarily for dental purposes. This mixer capsule has an activation mandrel which is located in the interior of the capsule and is anchored against the direction of ejection by means of holders in the interior of the capsule body, and a liquid compartment, which is accommodated in the interior of a ram and is sealed with respect to the activation mandrel by a destructible membrane. The activation mandrel fits flush into the empty vessel in the interior of the ram and seals the latter while the material is being forced out. While the material is being forced out in the longitudinal direction, the liquid passes through the thin capillary, which comes to lie in the interior of the activation mandrel, into the mixing space. It is explained that, even during the mixing operation in a vibration mixer and during the discharge of the compound via the ejection nozzle, a small residue of liquid, which is not precisely reproducible, always remains in the capillary. This impairs the quality of the results of mixing.

Consequently, the present invention is based on the object of providing an improved mixer capsule which avoids the abovementioned problems without impairing the desired results of mixing.

This object is achieved by a mixer capsule and a mixer unit which includes this mixer capsule as described in the claims.

The mixer capsule according to the invention has, inter alia, the following advantages:

The moveable body which is present in the mixer capsule serves not only to activate the capsule by destroying the separating device and to assist the mixing operation, but also as a displacement body during emptying.

Since, in the starting state, the body is situated in the main chamber, the activation preferably takes place automatically at the start of the mixing operation, by contrast to the activation steps known from the prior art, which have to be carried out manually.

Since, furthermore, the auxiliary chamber is separated from the main chamber by the separating device through which the body can penetrate, during the subsequent mixing operation it forms part of the mixing chamber itself. This ensures that the second component, which is contained in the auxiliary chamber, completely enters the mixture which is being formed.

Moreover, the unification of main chamber and auxiliary chamber advantageously increases the mixing volume available.

In the final phase of the discharge operation, the body assists with the virtually complete emptying of the interior of the mixer capsule which is formed by the main chamber and auxiliary chamber.

A further advantage is the small number and simple design of the components of the mixer capsule.

The moveable body is preferably of spherical design. The diameter of the ball preferably lies in the range from 4–10 mm, particularly preferably in the range from 5–8 mm.

The weight of the moveable body is adjusted to the condition of the separating device in such a manner that, during normal transport and normal handling, the separating device is not damaged by the moveable body. The separating device can only be penetrated once acceleration values of, for example, 100–500 g (1 g=9.81 ms$^{-2}$), preferably 200–400 g, which customarily occur in capsule mixer units are reached.

The auxiliary chamber is preferably in the shape of a hemisphere with a radius which is slightly larger than that of the body. This is favorable for the mixer capsule to be emptied with the minimum possible amount of residues.

It is advantageous if the separating device adheres to an annular surface, which delimits the auxiliary chamber, of the piston and the transition between the annular surface and the inner wall of the auxiliary chamber has a sharp-edged region.

This sharp-edged region preferably runs over a part of the circumference, preferably over substantially 60°–120°, particularly preferably from 70°–90°. The transition between annular surface and the inner wall of the auxiliary chamber is preferably rounded in the remaining region. This embodiment prevents the foil from tearing off altogether.

In a particular embodiment, the separating device has a desired breaking point, which contributes to controlled and reliable opening of the auxiliary chamber. The prior damage to the separating device or the preparation of a desired breaking point can be effected, for example, by radiation, such as laser radiation, mechanically by scoring or incision using a blade, or thermally by partial fusion or scoring using a heatable blade.

The preparation is preferably carried out only on the plastic part, which may be present, of the separating device, i.e. on the substrate material which is present on one or both sides of a metal layer or $SiO_x$-containing layer. As a result, the seal of the optionally present metal-containing or $SiO_x$-containing layer is maintained.

The preparation can be of any desired shape, but is preferably in a shape which prevents the separating device or parts of this device from tearing off after or during penetration of the separating device by the body. It has proven expedient for the separating device to be prepared in the form of two or more lines which cross one another in the axis of symmetry of the capsule.

In this case, the separating layer only bursts open at a defined location. This prevents the separating layer or parts of this layer from entering the mixture and impeding the discharge operation.

A further advantage of a desired breaking point produced in this way is that even relatively thick foils in the range from 50–80 μm, preferably 60–70 μm can be penetrated with little force (lower mass of the body).

The separating device is preferably in the form of a single-layer or multilayer film or foil, particularly preferably in the form of a composite film or foil or a sealing film or foil. The film or foil preferably comprises at least one metal layer, such as for example an aluminum layer, and at least one, if appropriate two, three or more, plastic layers.

Examples of suitable plastics are: PE, PP, PET, PTFE, PVC, polyamides.

Furthermore, instead of or in addition to the metal foil, the separating device may have plasma-polymerized layers, such as hydrocarbon-containing layers or ceramic barrier layers, such as $SiO_x$ layers.

The separating device is attached to the annular end face of the piston, for example by heat-sealing, adhesive bonding, ultrasonic welding or high-frequency welding.

Furthermore, to hold a third component, the separating device may, for example, be designed in the form of a film or foil cushion.

Advantageous materials for the piston of the mixer capsule include metals, such as anodized aluminum, glass, ceramic such as zirconia, plastics and/or— to reduce permeability—plastics which may have undergone metalization or vapor deposition or coating with other materials which have a barrier action. Examples of possible plastics include: PE, PP, PET, PTFE, PVC, EVA, polyamides.

Furthermore, combinations of the abovementioned materials, such as a metal insert, preferably made from aluminum, which is surrounded on the outside and on the inside by the plastic, are conceivable. Parts of this type can be produced using the injection-molding process.

The piston may be produced using a two-component injection-molding process. In this process, first of all, by way of example, an inlay is produced, around which, by way of example, PE is then injection-molded.

High-density plastics, such as PTFE, glass, ceramic, for example zirconia, metals which may be plastic-coated or stainless steel are suitable for the body of the mixer capsule.

The components which are contained in the main chamber, the auxiliary chamber and/or, if appropriate, in the separation device, include both liquids and solids, preferably in powder form. However, base substances in paste form are also possible.

The solids comprise inert fillers, such as finely ground quartz, $SiO_x$-containing substances, glass materials and surface-modified reactive fillers.

The liquids comprise in particular matrix-forming polymerizable substances, for example polyacids comprising acrylic acid derivatives, methacrylic acid derivatives and maleic acid derivatives, as well as copolymers thereof.

The discharge spout on the mixer capsule may be fitted eccentrically to the main chamber. It may also be advantageous to form one or more channels which open into the discharge spout. A design of this type may be expedient for undisturbed emptying of the mixer capsule.

Furthermore, the discharge spout is preferably of closeable design. Possible embodiments are described, for example, in EP-A-0 157 121, in which the discharge spout is pivotably mounted, so that it is closed or open depending on the position of the discharge spout. It is also conceivable to use a spout displacement cap in order to close the discharge spout.

Figure 2:
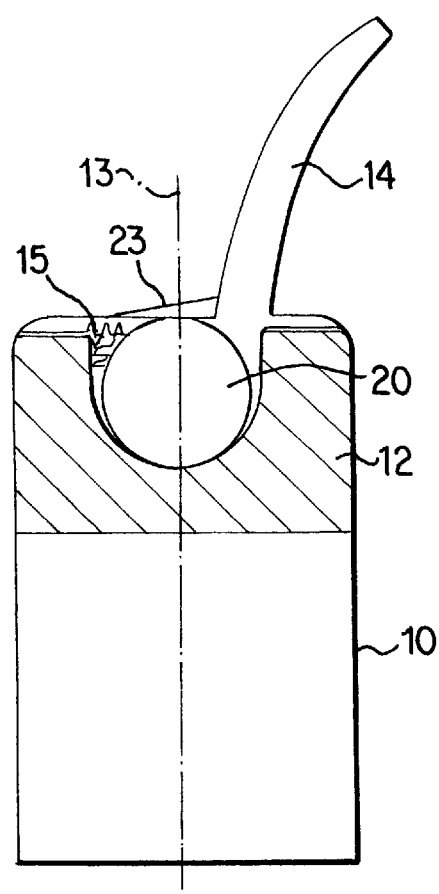
Figure 3:
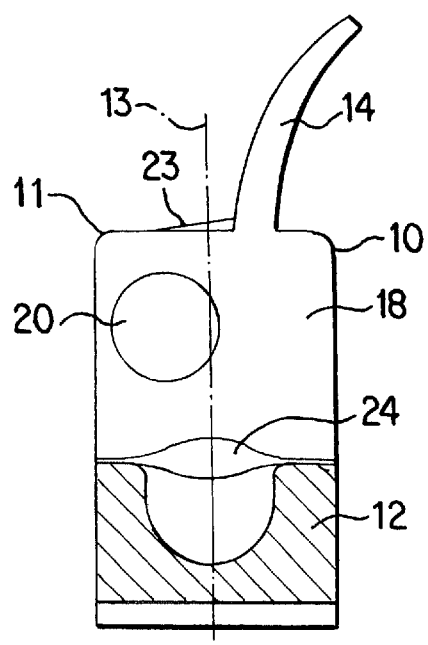

Preferred exemplary embodiments of the mixer capsule are explained below with reference to the drawings, in which:

FIG. 1 shows a longitudinal section through a mixer capsule in the starting state, FIG. 2 shows the same capsule at the end of the discharge operation, and FIG. 3 shows an illustration similar to that shown in FIG. 1 of a different embodiment.

In accordance with FIG. 1, the mixer capsule comprises a cylindrical cartridge 10, which is closed off at its front end by an end wall 11 and at its rear end by a piston 12. A curved discharge spout 14 is formed integrally on the end wall 11, eccentrically with respect to the cartridge axis 13. The discharge spout 14 may be of closeable design, for example by means of a displacement stopper.

The piston 12 has a significant axial wall thickness and is provided with a substantially hemispherical recess which is coaxial with respect to the cartridge axis 13 and is closed off by a separating device 16 attached to the annular front end face 15 of the piston 12. The separating device 16 separates the auxiliary chamber 17, which is formed by the recess, from the remaining interior of the cartridge, which is referred to here as the main chamber 18.

In the starting and/or stored state, the main chamber 18 contains a first component, which is, for example, in powder form, and the auxiliary chamber 17 contains a second component, which is for example in liquid form, of the mixture to be produced.

The mixer capsule furthermore includes a body 20 which can move freely, is preferably spherical and in the starting and/or stored state of the capsule is situated in the main chamber 18 and the radius of which is slightly smaller than the radius of the hemispherical recess which forms the auxiliary chamber 17. The body 20 and the auxiliary chamber 17 may also have different shapes which deviate from the spherical or hemispherical shape. The term freely moveable means that the body can in principle move in all directions without this movement being impeded by any form of guide rails.

The transition between the recess which forms the auxiliary chamber 17 and the annular end face 15 of the piston 12, as indicated in FIG. 1, is sharp-edged over an angular region 21 and is rounded in the remaining region 22.

The sharp edge may also be produced by a toothing.

The rounding prevents the separating device from tearing off this end-face inner edge region during the mixing operation, while the sharp-edged region 21 serves to form an initial tear on the separating device 16.

If, in another embodiment, the edge of the auxiliary chamber 17 is rounded all the way around, the separating device 16 can be made to tear by being preferentially overstretched at the desired breaking point as a result of the impact of the body 20 at the start of the mixing operation.

For use, the mixer capsule, which is supplied by the manufacturer in the condition illustrated in FIG. 1, is placed into a conventional capsule mixer unit, in which it is made to vibrate, for example, along the cartridge axis 13. In addition to purely translational movements of the capsule, rotary movements are also possible, if appropriate in combination with translational movements. In the process, the body 20 comes into contact with the separating device 16 and penetrates through it. As a result, main chamber 18 and auxiliary chamber 17 are connected to form a common mixing space. During the further mixing operation, the components are mixed together in this mixing space.

To discharge the finished mixture, the piston 12 is displaced forwards, in a commercially available application instrument, until it reaches the position shown in FIG. 2.

Since the recess which forms the auxiliary chamber 17 is of substantially hemispherical design and has a slightly larger radius than the spherical body 20, this body enters the recess and, in the process, acts as a displacement body. As a result, the mixing space can be substantially completely emptied.

If the auxiliary chamber 17 is arranged coaxially with respect to the cartridge axis 13 and the discharge spout 14 is arranged eccentrically, the body 20 does not impede the discharge operation.

To ensure that parts of the mixture which collect on the opposite side of the body 20 from the discharge spout also enter the spout 14, at least one channel 23 which deepens toward the discharge spout 15 may be molded integrally in the end wall 11 of the cartridge 10.

In a further variant (not shown), the discharge spout 14 may be arranged coaxially with respect to the cartridge axis 13.

So that the body 20 does not block the outlet for the finished mixture in this embodiment, it is preferable for a plurality of channels which run in different directions toward the discharge spout 14 to be formed integrally in the end wall 11 of the cartridge 10.

The exemplary embodiment shown in FIG. 3 differs from that shown in FIG. 1 in that a film or foil cushion 24, comprising two films or foils, is provided instead of the separating device 16, which cushion may contain a third component.

In a two-component variant, the underside of the cushion 24 may be thermoformed or deep-drawn down to the base of the piston. In this way, it is possible to produce an improved diffusion barrier with respect to the piston.

When the mixing operation begins, the body 20 penetrates through the film or foil cushion 24, so that all three components can be mixed in the mixing space which is then formed as a combination of main chamber 18 and auxiliary chamber 17.

As shown in the drawing, the piston 12 has a substantial wall thickness. This has the advantage that the piston 12 presents a good diffusion barrier even if, for cost reasons, it is made from plastic.

LIST OF REFERENCE SYMBOLS

10 Cartridge
11 End wall
12 Piston
13 Cartridge axis
14 Discharge spout
15 End face
16 Film or foil
17 Auxiliary chamber
18 Main chamber
20 Body
21 Sharp-edged region
22 Rounded region
23 Channel
24 Film or foil cushion

What is claimed is:

1. A mixer capsule, comprising:
   a main chamber for holding a first component, said chamber having a discharge spout at one end and being sealed at its other end by means of a piston,
   an auxiliary chamber in the piston for holding a second component,
   a body disposed in the main chamber and which can move freely therein, and
   a separating device which separates the auxiliary chamber from the main chamber and through which the body can penetrate from the main chamber to the auxiliary chamber when the capsule is agitated, the auxiliary chamber and the body being configured in such a way that when the components are to be discharged, the body can enter the auxiliary chamber as a displacement body.

2. The mixer capsule as claimed in claim 1, in which the body is spherical.

3. The mixer capsule as claimed in claim 1, in which the separating device contains at least one desired breaking point.

4. The mixer capsule as claimed in claim 1, in which the discharge spout is disposed eccentrically to the main chamber.

5. The mixer capsule as claimed in claim 4, further comprising at least one channel which opens into the discharge spout formed in an end wall of the main chamber which is provided with the discharge spout.

6. The mixer capsule as claimed in claim 1, in which the separating device acts as a cushion for holding a third component.

7. The mixer capsule as claimed in claim 1, in which the separating device comprises at least one of a metal-containing foil, a hydrocarbon-containing layer, and a ceramic barrier layer.

8. The mixer capsule as claimed in claim 7, wherein the ceramic is $SiO_x$.

9. The mixer capsule as claimed in claim 1, in which the piston comprises a material selected from the group consisting of metal, glass, ceramic, plastic, plastic-coated metal, plastic-coated glass, plastic-coated ceramic, and metalized plastic.

10. The mixer capsule as claimed in claim 1, in which the body comprises a material selected from the group consisting of glass, ceramic, PTFE, plastic-coated metal, and stainless steel.

11. The mixer capsule as claimed in claim 1, wherein at least one of the first and second component is a solid or a liquid.

12. The mixer capsule as claimed in claim 1, wherein said components are dental materials.

13. A mixer unit including the mixer capsule as claimed in claim 1.

14. A mixer capsule comprising a main chamber for holding a first component, said chamber having a discharge spout at one end and being sealed at its other end by means of a piston, an auxiliary chamber in the piston for holding a second component, a spherical body disposed in the main chamber and which can move freely therein, and a separating device which separates the auxiliary chamber from the main chamber and through which the body can penetrate, the auxiliary chamber and the body being configured in such a way that when the components are to be discharged, the body can enter the auxiliary chamber as a displacement body, wherein the auxiliary chamber is substantially in the shape of a hemisphere with a radius which is slightly larger than that of the body.

15. A mixer capsule comprising a main chamber for holding a first component, said chamber having a discharge spout at one end and being sealed at its other end by means of a piston, an auxiliary chamber in the piston for holding a second component, a body disposed in the main chamber and which can move freely therein, and a separating device which separates the auxiliary chamber from the main chamber and through which the body can penetrate, the auxiliary chamber and the body being configured in such a way that when the components are to be discharged, the body can enter the auxiliary chamber as a displacement body, wherein the auxiliary chamber has an inner wall, the piston comprises an annular surface which delimits the auxiliary chamber with a transition between the annular surface and the inner wall of the auxiliary chamber, the transition between the annular surface and the auxiliary chamber having at least one of a sharp-edged region and a rounded region, and wherein the separating device adheres to said annular surface.

* * * * *